United States Patent
Tipler et al.

(10) Patent No.: US 7,662,630 B2
(45) Date of Patent: Feb. 16, 2010

(54) METHOD FOR VERIFYING THE INTEGRITY OF THERMAL DESORPTION SAMPLING TUBES

(75) Inventors: Andrew Tipler, Trumbull, CT (US); Frank DeLorenzo, Stratford, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 211 days.

(21) Appl. No.: 11/285,914

(22) Filed: Nov. 23, 2005

(65) Prior Publication Data
US 2006/0094118 A1    May 4, 2006

Related U.S. Application Data

(63) Continuation of application No. PCT/US2004/016555, filed on May 24, 2004.

(60) Provisional application No. 60/472,854, filed on May 23, 2003.

(51) Int. Cl.
*G01N 35/00* (2006.01)

(52) U.S. Cl. ............... 436/43; 436/180; 422/63; 422/64; 422/65; 422/99; 422/100

(58) Field of Classification Search .......... 436/43, 436/180; 422/63–65, 99–101
See application file for complete search history.

(56) References Cited

U.S. PATENT DOCUMENTS

| | | | |
|---|---|---|---|
| 4,600,559 A | 7/1986 | Hiatt | 422/89 |
| 4,650,499 A | 3/1987 | Scott | 55/18 |
| 5,337,619 A | 8/1994 | Hodgins et al. | 73/863.11 |
| 5,661,224 A | 8/1997 | Walsh | 73/1.03 |
| 5,792,423 A * | 8/1998 | Markelov | 422/83 |
| 5,847,291 A * | 12/1998 | Green et al. | 73/863.33 |
| 5,922,106 A * | 7/1999 | Mowry et al. | 95/87 |
| 5,970,804 A | 10/1999 | Robbat, Jr. | 73/863.12 |
| 6,162,282 A | 12/2000 | Walters et al. | 95/82 |
| 2002/0148353 A1 | 10/2002 | Seeley | 95/86 |

FOREIGN PATENT DOCUMENTS

| | | |
|---|---|---|
| EP | 0 306 332 | 3/1989 |
| EP | 0 554 604 | 8/1993 |

OTHER PUBLICATIONS

Camel V. et al. "Trace Enrichment Methods for the Determination of Organic Pollutants in Ambient air" Aug. 25, 1995 Journal of Chromatography; A. Elsevier Science, NL, vol. 710, No. 1, pp. 3-19.
PCT International Search Report, Dec. 21, 2004, 3 pages.
(Performance Evaluation of a Thermal Desorption/Gas Chromatographic/Mass Spectrometric Method for the Characterization of Waste Tank Headspace Samples) C.-Y. Ma, et al. 1997 Environmental Science Technology, vol. 31, pp. 853-859, Figure 1, table 1.
(AnaCheck Prespiked QC Sorbents) Anonymous, SKC Product Data Bulletin, retrieved on Nov. 21, 2005, URL:www.skcinc.com.

* cited by examiner

*Primary Examiner*—Jill Warden
*Assistant Examiner*—Jyoti Nagpaul
(74) *Attorney, Agent, or Firm*—St. Onge Steward Johnston & Reens LLC

(57) ABSTRACT

An analyte of a sample is transferred to an analytical instrument by introducing a quantity of a compound of a standard material into a vessel containing an adsorbent material; introducing a quantity of the analyte of the sample into the vessel; and transferring the analyte of the sample and the compound of the standard material to the analytical instrument.

16 Claims, 8 Drawing Sheets

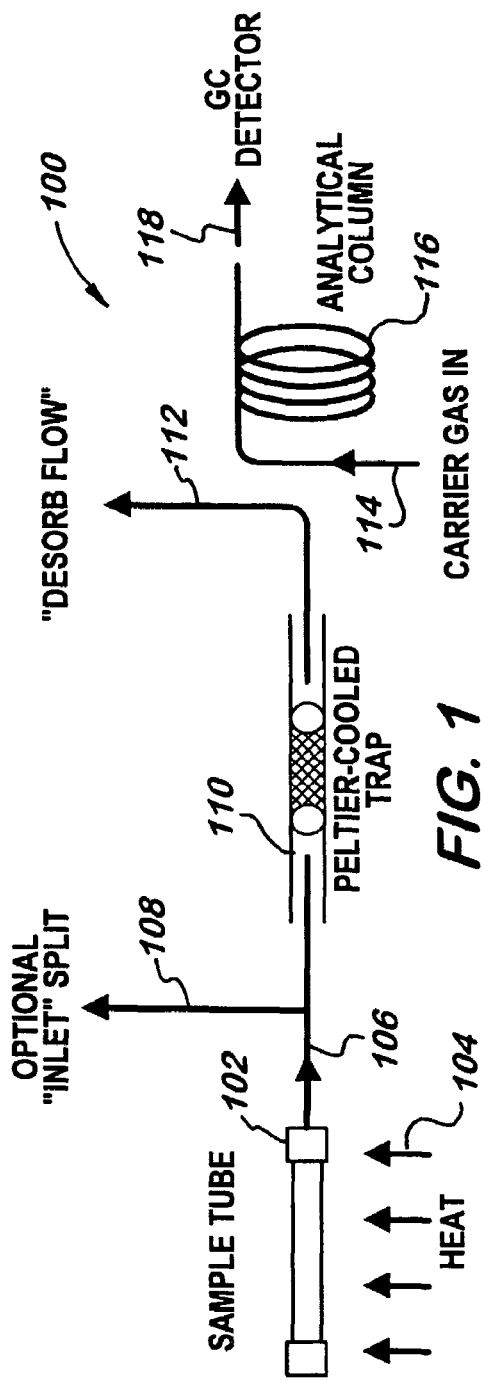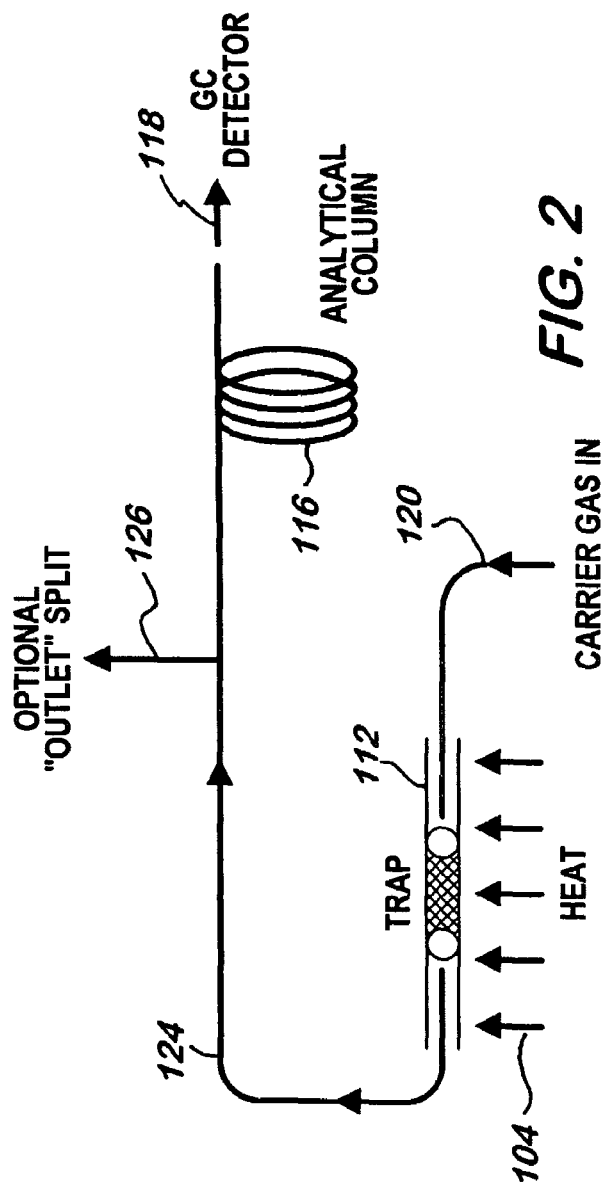

METHOD FOR VERIFYING THE INTEGRITY OF THERMAL DESORPTION SAMPLING TUBES

PRIOR APPLICATIONS

This application is a continuation of pending International Patent Application No. PCT/US2004/016555 filed on May 24, 2004 which designates the United States, and which claims the benefit of, under 35 U.S.C. §119(e), U.S. Provisional Patent Application Ser. No. 60/472,854 filed May 23, 2003 which is incorporated herein by reference as if set forth at length.

FIELD OF THE INVENTION

This invention relates to a method and apparatus for verifying the integrity of thermal desorption sampling tubes.

BACKGROUND OF THE INVENTION

The Environmental Protection Agency (EPA) establishes standards against which the relative abundance of compounds in samples may be compared and thus the compound may be determined. For example, through the use of standard compounds such as bromoflurobenzene (BFB) and decaflurotriphenylphosphine (DFTPP) volatile and semi-volatile organic compounds in water may be analyzed. The standard compounds are injected into a gas chromatograph-mass spectrometer (GC-MS) system under standard conditions. The resulting spectra are examined to determine the performance include ion mass resolution, relative ion abundance and mass accuracy over the range of ion masses analyzed. The mass spectrometer is tuned to obtain a spectrum for BFB or DFTPP that meets EPA standards. Commercial mass spectrometers must be capable of being tuned to meet these EPA standards in order to accurately determine the presence of specific compounds in a sample.

In the analysis of air samples and other gaseous matrices, a popular method of collecting any volatile organic compound (VOC) present in the sample is to pump the sample, at a fixed rate, through a tube packed with a suitable adsorbent material. This is known as pumped sampling. An alternative method to pumped sampling is to allow VOCs in the air to migrate into the tube through natural diffusion. This is known as diffusive or passive sampling.

Once the VOCs have been collected, they are vaporized by heating the tube in a thermal desorption instrument. A flow of an inert gas, such as Helium or Nitrogen, is applied to the tube to sweep the VOC vapor into a gas chromatographic (GC) column for separation and analysis. An additional trap is usually employed in the thermal desorption instrument to effect a pre-concentration of the VOC analytes prior to their injection into the GC. FIGS. 1 and 2 illustrate this technique.

However, if proper care is not taken in the process of handling, sampling, storing and analyzing the tubes, errors may be introduced into the analytical results because of sample leakage from the tube or ingress of compounds from the storage equipment. Unfortunately, there has been no mechanism to ascertain whether such leakage has occurred and so, the validity of the data must be assumed.

Thus, it would be advantageous to provide a method and apparatus for verifying the integrity of thermal desorption sampling tubes.

SUMMARY OF THE INVENTION

A thermal desorption system is configured with an internal standard gas (IS) addition accessory. This accessory is used to deliver a volume (typically 0.5 mL) of a pressurized standard gas into a clean (conditioned) sample tube prior to sampling, desorption and analysis. The standard gas contains one or more compounds known not to be present in the sample but which are of a similar concentration and chemistry as the sample compounds. In the final chromatography, the peaks from these standard gas compounds are identified, quantified and used to make a ratiometric correction to the quantitative results from the analyte compounds.

This technique compensates for instrumental variations that may affect the analytical results—both the standard gas compound and each analyte are subjected to the same variations and so their relative responses provide a more valid quantitative measure of the amount of analyte present.

To provide a full analytical control, the standard gas is added before the tube is used to take a sample. The standard gas addition accessory may be modified to add the gas standard to clean adsorbent tubes but not apply the thermal desorption step. In this way, for example, a full set of 50 sample tubes in an automated thermal desorption (ATD) system can be quickly loaded with the IS.

BRIEF DESCRIPTION OF THE DRAWINGS

FIG. 1 is a schematic drawing showing a thermal desorption apparatus for tube desorption;

FIG. 2 is a schematic drawing showing a thermal desorption apparatus for trap desorption;

DETAILED DESCRIPTION OF THE INVENTION

FIG. 1 is a schematic drawing showing a thermal desorption apparatus for tube desorption. FIG. 2 is a schematic drawing showing a thermal desorption apparatus for trap desorption.

Figure 3:
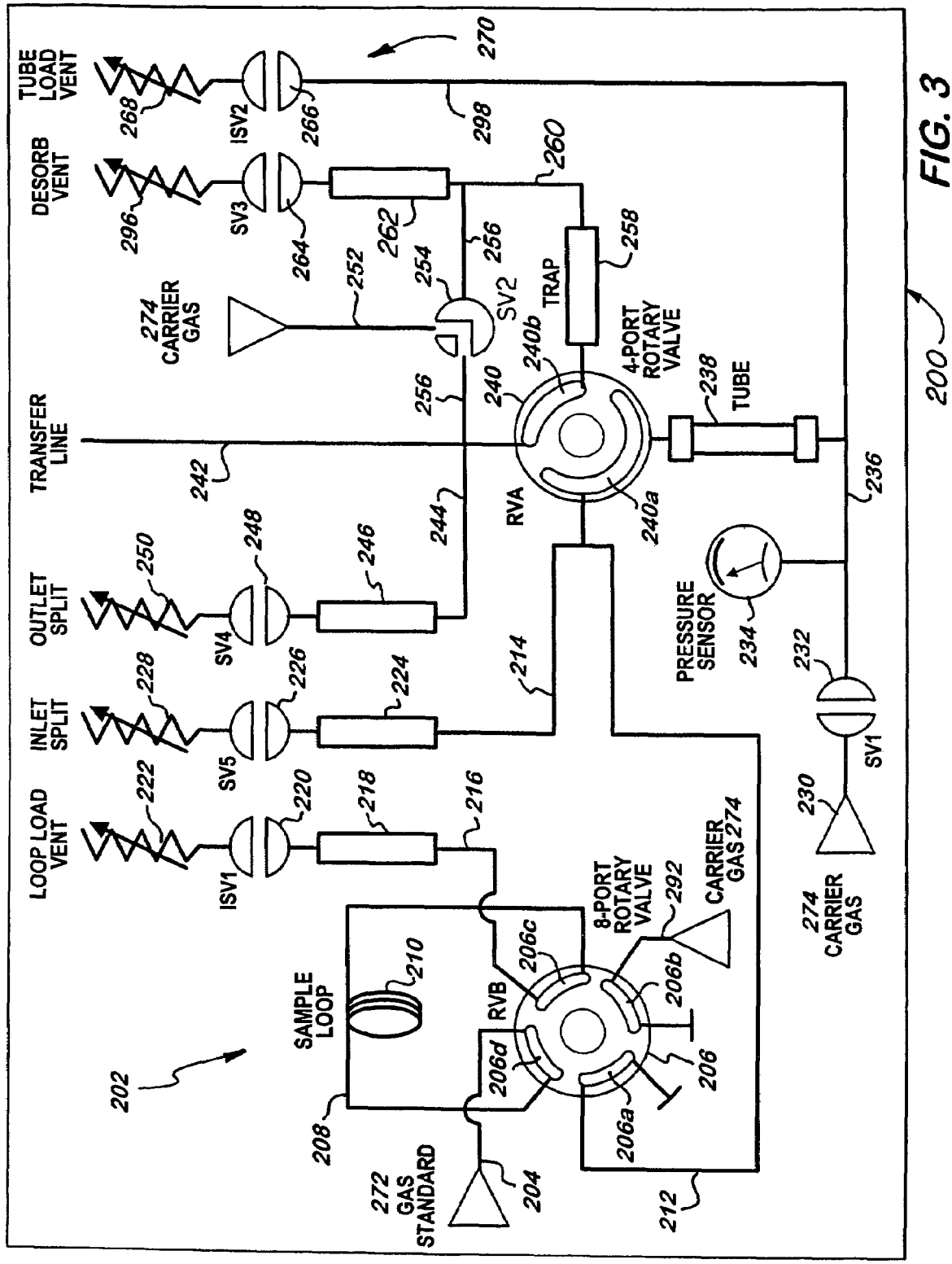
FIG. 3 is a schematic drawing showing a thermal desorption apparatus with an internal standard.

A thermal desorption system is shown generally in FIG. 3 at 200. The thermal desorption system 200 comprises a first rotary valve (RVB) 206 which includes a set of ports 206a, 206b, 206c, 206d. The ports 206a, 206b, 206c, 206d include a fluid inlet segment and a fluid outlet segment. The first rotary valve 206 is in fluid communication with a standard gas 272 via a conduit 204 at port 206d. A conduit 208, which includes a sample loop 210, provides fluid communication between port 206d and port 206c of the first rotary valve 206. A loop load vent 216, which includes a filter 218, such as a charcoal filter, a valve 220 (ISV1) and a flow regulator 222, vents the first rotary valve 206 from port 206c. The first rotary valve 206 is also in fluid communication with a carrier gas 274 via a conduit 292 at port 206b.

The thermal desorption system 200 further comprises a second rotary valve (RVA) 240 which includes a set of ports 240a, 240b. The ports 240a, 240b include a fluid inlet segment and a fluid outlet segment. The second rotary valve 240 and the first rotary valve 206 are in fluid communication with one another at the ports 240a and port 206a respectively via a conduit 212. An inlet split 214, which includes a filter 224, a valve 226 (SV5) and a flow regulator 228 vents the second rotary valve 240 from port 240a. The second rotary valve 240 is in fluid communication with a carrier gas 274 via a conduit 236 and a sample tube 238 at port 240a. The conduit 236 includes a valve 232 (SV1) and a pressure sensor 234. A tube load vent 298 vents the sample tube 238 and includes a valve 266 (ISV2) and a flow regulator 268. The second rotary valve 240 is also in fluid communication with a trap 258 via a conduit 260. The conduit 260 includes a filter 262, a valve 264 (SV3) and a desorption vent 296 and vents the second rotary valve 240 from port 240a. The conduit 260 also provides fluid communication with an outlet split 244 and a conduit 256 via a valve 254 (SV2). The valve 254 is in turn in fluid communication with a carrier gas 274 via a conduit 252. The outlet split 244 which includes a filter 246, a valve 248 (SV4) and a flow regulator 250, vents the second rotary valve 240. A transfer line 242 is connected to the second rotary valve 240 at port 240b and provides fluid communication with a gas chromatograph (not shown).

In FIGS. 3-7, the first rotary valve 206 and second rotary valve 240 are such that by the rotation thereof, the various aforementioned ducts or fluid conduits are connected to either a fluid inlet segment or a fluid outlet segment of ports 206 a,b,c,d and ports 240 a,b so as to control or direct, in conjunction with valves 220, 226, 248, 264, 266, 254, 232, the flow of the standard gas 272, a sample gas and the carrier gas 274 through the thermal desorption system 200.

Figure 4:
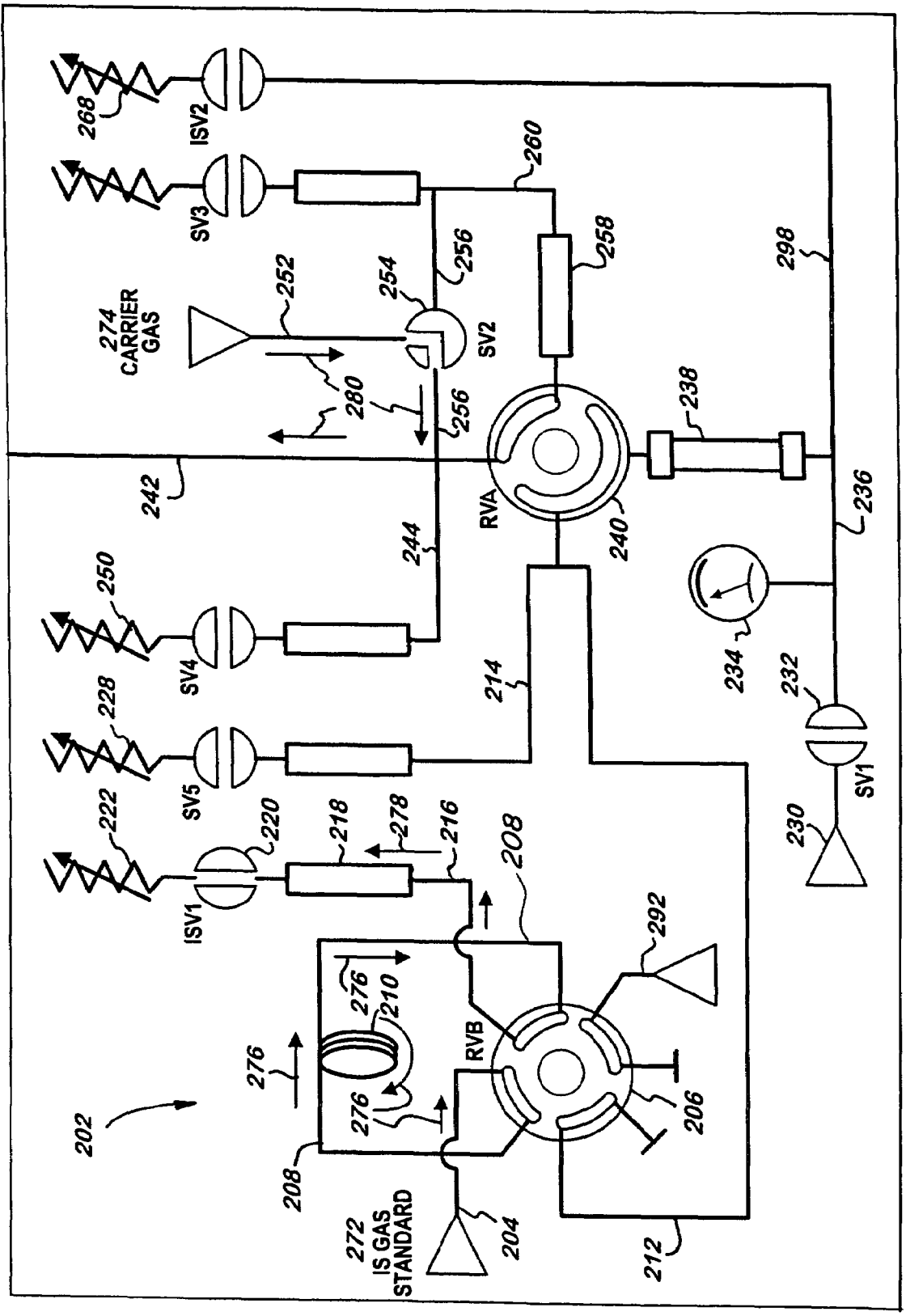
FIG. 4 is a schematic drawing showing a thermal desorption apparatus with the internal standard of FIG. 3 showing an arrangement for a sample loop fill.

In FIG. 4, a standard gas 272, such as Nitrogen or Helium, is allowed to flow into the first rotary valve 206 via conduit 204, thence in a forward direction through conduit 208 and the sample loop 210, back to the first rotary valve 206, thence to atmospheric pressure via the loop load vent 216. This flow is regulated by flow regulator 222 so as to collect a fixed quantity of a known standard compound or compounds entrained in a standard gas 272 in the sample loop 210 or to maintain a fixed mass flow rate of the standard gas 272 through the sample loop 210. Carrier gas 274 is allowed to flow into the thermal desorption system 200 through conduits 252, 256, 242 in a stand by mode. The flow of the standard gas 272 and the carrier gas 274 through the thermal desorption system 200 is seen in FIG. 4 by the flow arrows 276, 278 and 280 respectively.

Figure 5:
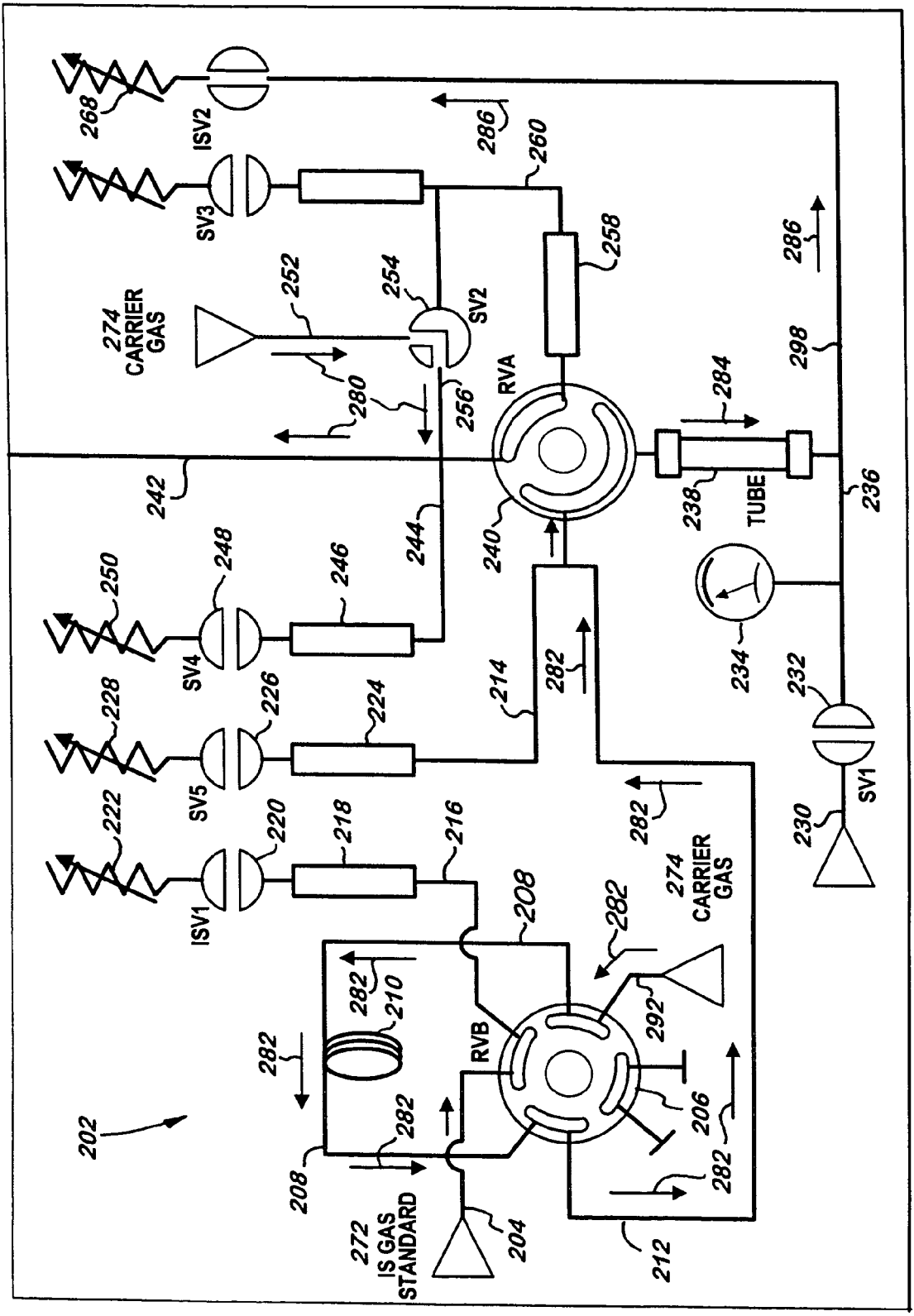
FIG. 5 is a schematic drawing showing a thermal desorption apparatus with the internal standard of FIG. 3 showing an arrangement for a tube load.

In FIG. 5, upon rotation of the first rotary valve 206, the carrier gas 274 is allowed to flow into the first rotary valve 206 via conduit 292. The carrier gas 274 mixes with the previously loaded fixed quantity of standard gas 272 in the sample loop 210 and the mixture is directed through the sample loop 210 in a reverse direction via conduit 208 back into the first rotary valve 206 thence to the second rotary valve 240 via conduit 212. From the second rotary valve 240 the standard gas/carrier gas mixture is directed through the sample tube 238 containing an adsorbent material. The carrier gas is thence directed from the sample tube 238 to the tube load vent 298 via valve 266 and flow regulator 268. The flow of the standard gas/carrier gas mixture and carrier gas is seen in FIG. 5 by the flow arrows 282, 284 and 286 respectively.

As a result of the aforesaid gas flow, the fixed quantity of standard compounds is collected from the standard gas via adsorption in the sample tube 238 containing an adsorbent such as TENAX TA™, TENAX GR, Chromosorb™ 102, Chromosorb™ 106, Spherocarb, carbon molecular sieves, charcoal, Carbotrap™, Carbopack C™, Carbopack Y™ Carbopack B™, Poropak Q or Poropak N. Alternatively, a metered flow rate of a gas containing the standard compounds is allowed to pass through the desorption system 200 and thus the sample tube 238.

Figure 6:
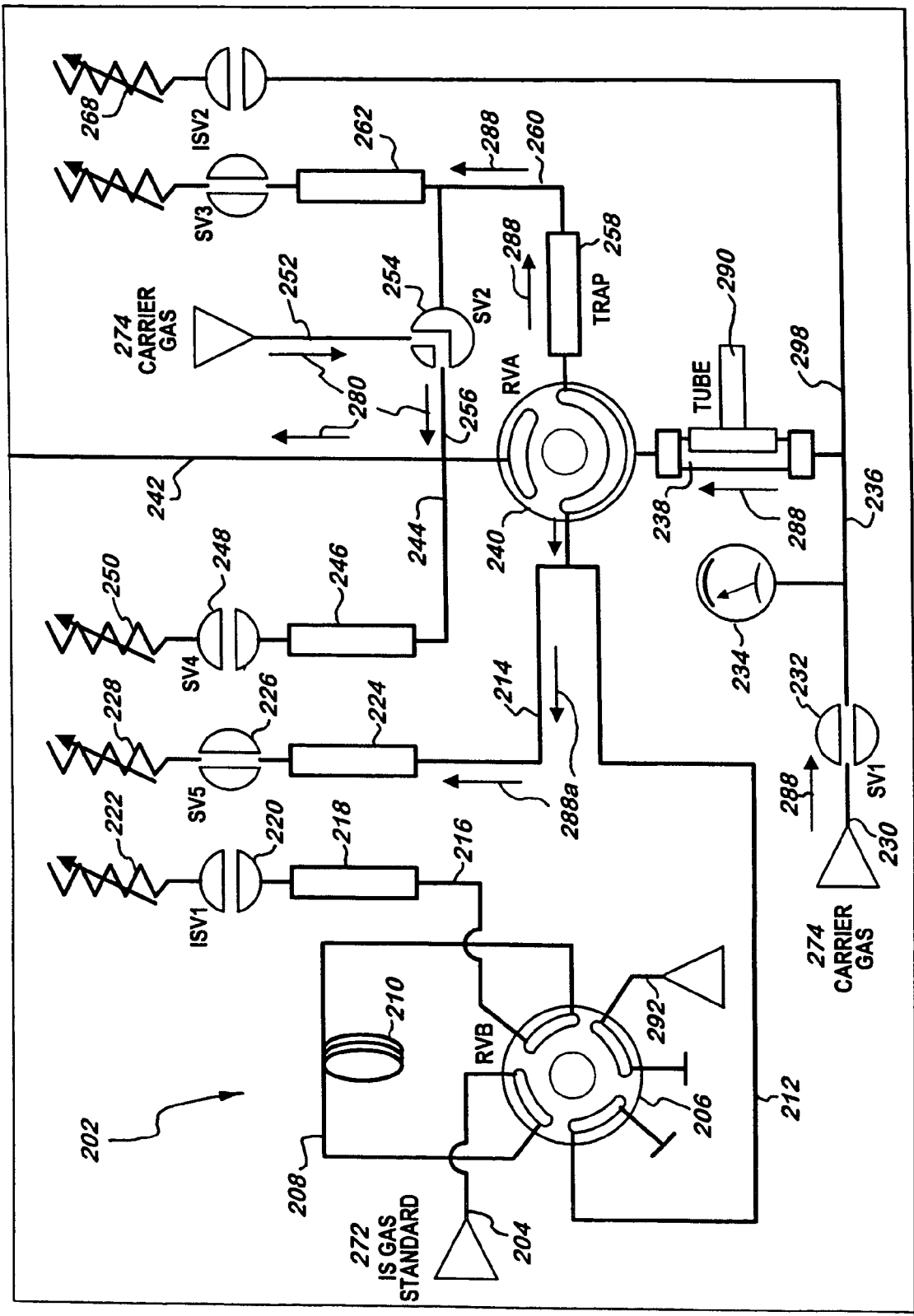
FIG. 6 is a schematic drawing showing a thermal desorption apparatus with the internal standard of FIG. 3 showing an arrangement for a tube desorption.

In FIG. 6, upon rotation of the first rotary valve 206 and the second rotary valve 240, the first rotary valve 206, including sample loop 210, conduit 208 and conduit 212, is or may be isolated from the second rotary valve 240. With the aforesaid isolation, the sample tube 238, containing a known quantity of a standard compound, may be removed and a gaseous sample, possibly containing analytes, may now be collected in the sample tube 238 at a remote location. The sample tube 238 is later returned to the thermal desorption system 200 and a carrier gas 274 is allowed to flow into the thermal desorption system 200 via conduit 230. The carrier gas 274 is directed through the sample tube 238, the second rotary valve 240, through a trap 258, thence to a desorption vent 260 via filter 262, valve 264 and flow regulator 296. This flow is seen by flow arrows 288. An operator may also direct a portion of the carrier gas 274 to inlet split 214 thence to filter 224, valve 226 and flow regulator 228. This flow is seen by flow arrows 288a. Heat 290 may be added to the sample tube 238 as the carrier gas is directed therethrough.

As a result of the previous gas flow, a desorption process takes place in the sample tube 238 whereby the standard compounds and the sample analytes, are carried in flow to the trap 258 by the carrier gas 274. The desorption may be a thermal desorption. The analyte entrained in the sample gas and the standard compounds in the standard gas are collected in the trap 258 which may contain an adsorbent, or be cooled, or both.

Figure 7:
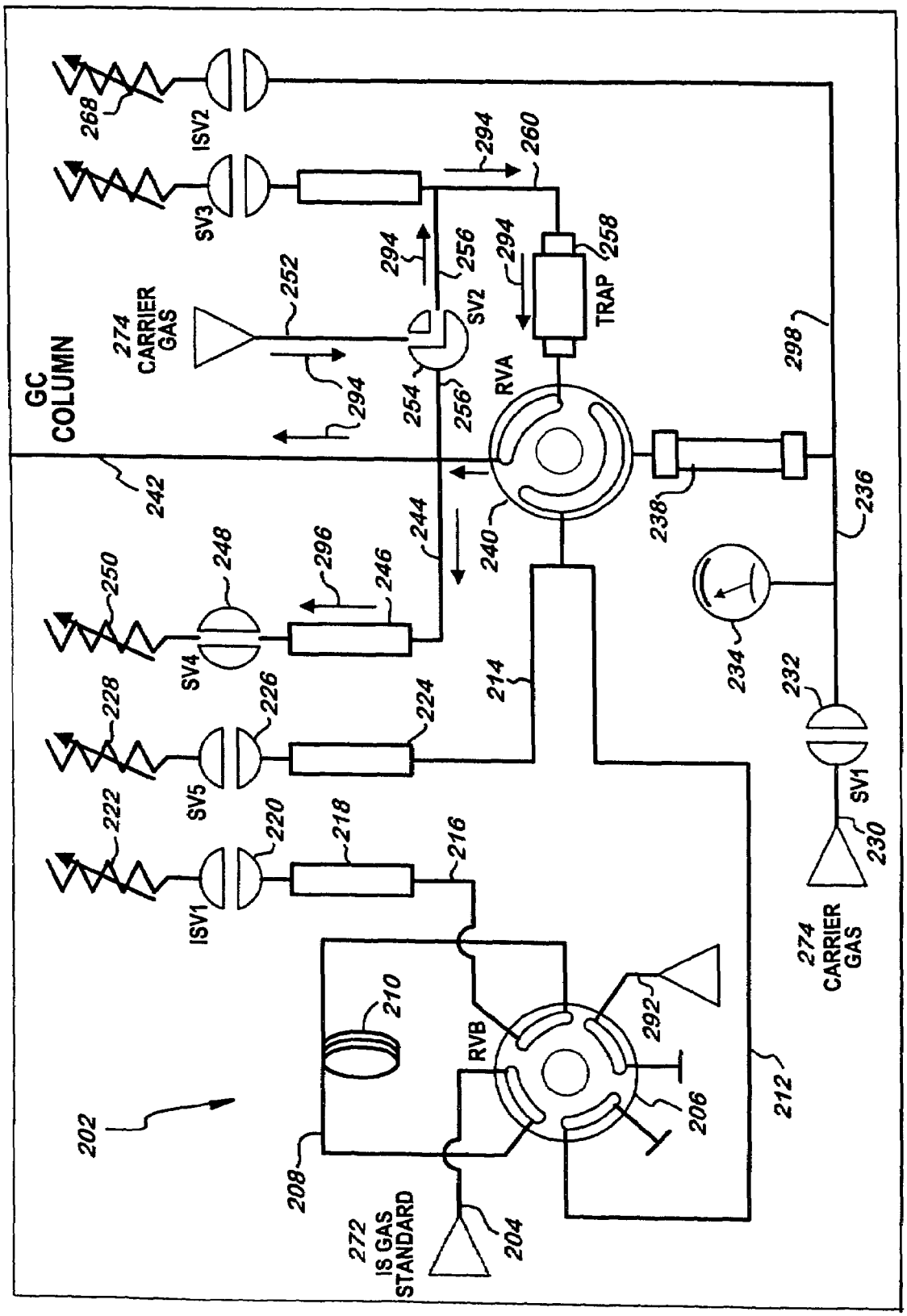
FIG. 7 is a schematic drawing showing a thermal desorption apparatus with the internal standard of FIG. 3 showing an arrangement for a trap desorption.

In FIG. 7, upon rotation of the second rotary valve 240 and valve 254, carrier gas 274 is allowed to flow into the thermal desorption system 200 via conduit 252. The carrier gas 274 is further directed through conduits 276, 260 thence through the trap 258 in a reverse direction and thence through the second rotary valve 240. In the second rotary valve 240 the carrier gas is directed to the gas chromatograph along the transfer line 242 and/or to the outlet split 244, thence through the filter 246, valve 248 and flow regulator 250. This flow pattern can be seen by the flow arrows 294 and 296.

As a result of the previous gas flow, a desorption process takes place in the trap 258. Such desorption process may include thermal desorption by, for example, the fast addition of a quantity of heat to an initially very cold (e.g., about −25° C.) trap 258 as the carrier gas is directed back through the trap 258 in a reverse direction. The sample analytes and standard compounds are thus, physically closer together as they pass to the gas chromatograph. Thus, analytes from the sample gas and standard compounds from the standard gas are released from the adsorbent contained within the trap 258. The sample analytes and the standard compounds are carried in flow with the carrier gas 274 to the gas chromatograph for analysis.

Figure 9:
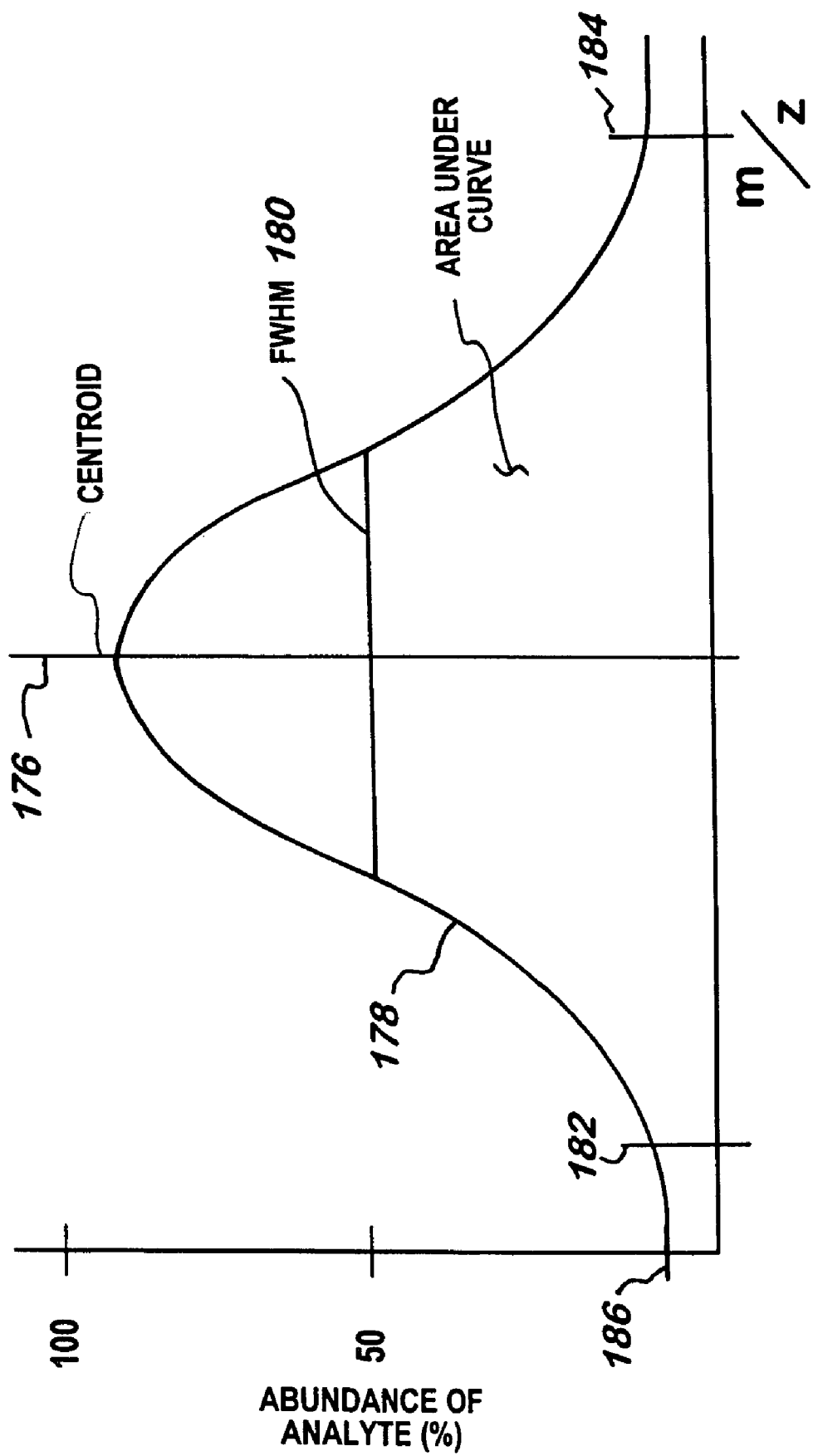
FIG. 9 shows a mass spectrographic peak of the abundance of an analyte of interest as a function of mass-to-charge ratio, m/z.

Adding the standard gas to the sample tube before the sample tube is used to collect a sample gas allows one to assess the integrity of entire analysis of the sample gas. However, this does not allow for the discrimination of errors due to sampling, handling and storing of the sample gas from those errors arising from instrumental variances. Such discrimination can be achieved by first adding a standard gas before introducing the sample gas and adding a second, different, standard gas after sampling, though prior to tube desorption. The ratio of the areas of the chromatographic peaks from each standard gas is a true measure of sample integrity. The addition of the second standard gas can be used to correct for instrumental variances. The second standard gas may be a compound such as bromoflurobenzene (BFB) for tuning a mass spectrometer. In the use of multiple standard gases, less volatile standard gases will be more strongly retained and may be used as a reference against volatile standard gases which are more likely to be lost from the tube in the event of a tube leak. Thus, the ratio of the area of the chromatographic peaks of the more volatile to less volatile gases will provide a measure of sample integrity. FIG. 9 shows a mass spectrographic peak 178 of the abundance of an analyte as a function of mass-to-charge ratio, m/z. The figure shows a continuum of data with a centroid 176 and full width at half maximum (FWHM) 180.

Compounds in a standard gas should be selected that are well separated from compounds in the sample gas so that the standard gas does not interfere or co-elute with the compounds of the sample gas. For example, if benzene, toluene or xylene are being analyzed, deuterated toluene (toluene-D8) can be used as the standard gas. Toluene-D8 is chemically almost the same compound as toluene, except that the hydrogen atoms have been replaced with deuterium atoms, which adds 8 amu to the total mass of the molecule. This makes the standard gas easy to distinguish in a chromatogram run on a GC-MS system. Toluene-D8 does not exist in nature and so there is no interference with naturally occurring compounds.

In the method of the present invention, the analyte(s) in the sample gas and the compound(s) in the standard gas are directed to the GC-MS where they are separated in the gas chromatograph and their mass spectra determined in the mass spectrometer. The mass spectrum of a compound in the standard gas (standard compound) is compared to a known mass spectra of the compound of the standard gas. If the mass spectrum of the standard compound is other than the aforesaid known mass spectra of the standard compound, then an analyst may determine whether the sampling process has been compromised and whether to repeat the process of first introducing a first quantity of a standard gas into a first vessel containing an adsorbent material; then introducing a quantity of the sample into the first vessel; and transferring the analyte of the sample and a compound of the standard gas to the analytical instrument. Determining the mass spectrum of the standard compound comprises comparing intensities of individual mass spectra of the compound of the standard gas to a standard mass spectra of the compound of the standard gas.

Yet further, a second quantity of a compound in a standard gas may be introduced into the first vessel wherein the composition of the second standard gas is different than that of the first standard gas. Introducing a second quantity of a compound in a standard gas into the first vessel comprises introducing the second quantity of a compound in a standard gas into the first vessel after introducing a quantity of the sample gas into the first vessel and before transferring the compound in the sample gas and a compound in the plurality of standard gases to the analytical instrument.

Thus, as described above, a method of verifying the integrity of a thermal desorption sample tube is disclosed. The method comprises loading a precise amount of a known standard gas, containing a compound similar in chemical or molecular structure to a suspected analyte, into a vessel or container. A sample tube, containing a known adsorbent material, is conditioned or made clean by allowing an inert gas, such as Nitrogen or Helium, to flow therethrough while the tube is heated. The method further comprises loading a carrier gas into the loop. The carrier gas carries the compounds in the standard gas in flow to the sample tube. The compounds in the standard gas adhere to the adsorbent material, which may be at ambient temperature, while the carrier gas passes through the sample tube to vent. A precise amount of a known compound in the standard gas now resides in the sample tube on the adsorbent material. An analyst may now take the sample tube into the field and collect a quantity of a sample gas which may contain a suspected analyte. The sample tube will then contain a known amount of a known compound from the standard gas, an unknown amount of an unknown sample, plus an unknown amount of an analyte and a known adsorbent material. The tube is reinstalled in the thermal desorber and the flow of the carrier gas is reversed through the sample tube at ambient temperature. The carrier gas, the standard compounds and the sample flow, in a forward direction, through a cold trap containing a known adsorbent material. The carrier gas flows through the trap and is vented away and the sample and standard compounds are retained in the trap. The carrier gas is allowed to flow in a reverse direction while heat is rapidly applied to the trap, helping to clean the trap. When heat is applied to the trap the adsorbent material therein releases molecules of analytes in the sample gas and the carrier gas flushes the trap of the standard compounds and the sample molecules (including any analytes). The flow of the carrier gas plus the standard compounds and the sample with the analyte is then directed to a gas chromatograph for analysis. The above method may now be repeated with the exception that an analyst may add a precise amount of a second known standard compound in a gas to the loop. If so, the areas of the relevant chromatographic peaks can be ratioed to verify the integrity of the sample tube.

Thus, based upon the foregoing description, a method of transferring a quantity of a sample, or possibly a suspected analyte thereof, to a gas chromatographic instrument for analysis is disclosed. The method comprises introducing a quantity of a standard material into a first vessel containing an adsorbent material; introducing a quantity of the sample into the first vessel; and transferring the sample and the standard material to the analytic instrument.

Figure 8:
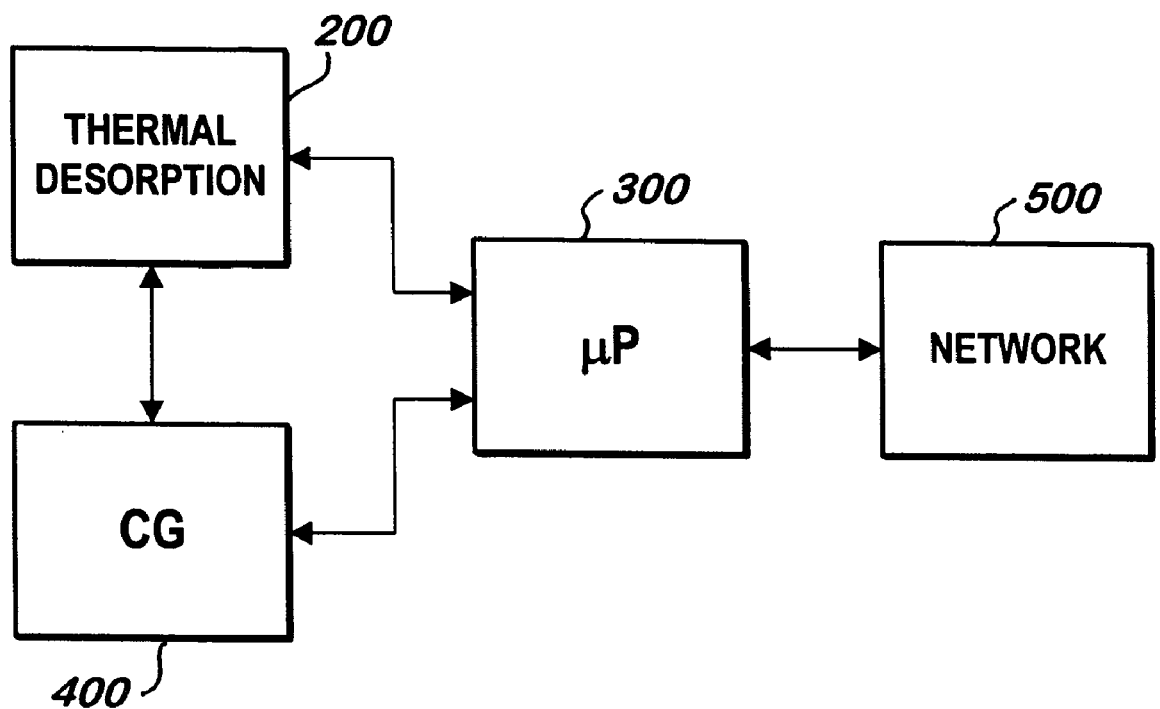
FIG. 8 is a schematic diagram of the thermal desorption apparatus of FIG. 3 in communication with a computer network and a gas chromatograph.

As seen in FIG. 8, the method described above may be accomplished in the thermal desorption system 200 under the control of a computer 300. The computer 300 may also be connected to a remote computer through a computer or communications network 500 such as an intranet or the Internet and to a gas chromatograph (GC) 400 for analysis of the sample. The computers are configured so as to send, receive, store and otherwise process signals indicative of the concentration of compounds or elements in a sample and thus the veracity of the integrity of a sample tube in a thermal desorption method.

In the present invention, a storage medium is encoded with machine readable program code for effecting a method of verifying the integrity of a thermal desorption sampling tube. The program code includes instructions for causing a thermal desorption system to transfer an analyte of a sample to an analytical instrument by first introducing a first quantity of a standard material into a first vessel containing an adsorbent material; then introducing a quantity of the sample into the first vessel; and transferring the analyte of the sample and a compound of the standard material to the analytical instrument.

In the foregoing description it should be understood that any reference to first, second, front, rear, etc. or any other phrase or terminology indicating the relative position of one element or device with respect to another is for the purposes of explanation of the invention and, unless otherwise noted, is not to be construed as limiting the invention. Furthermore, while the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment, but that the invention will include all embodiments falling within the scope of any appended claims.

What is claimed is:

1. A method of transferring an analyte of a sample to an analytical instrument, the method comprising:
   introducing a first quantity of a standard material into a first vessel containing an adsorbent material;
   introducing a quantity of the sample into the first vessel;
   transferring the analyte of the sample and a compound of the standard material to the analytical instrument;
   selecting a standard having chromatographic detection characteristics indicative of the sample to be analyzed;
   introducing the standard into a vessel placed at a location of thermal desorption;
   transporting the vessel to a site remote from and separate from the location for collecting a sample, wherein the sample is mixed with the standard;
   transporting the vessel to the location;
   introducing the sample and standard into a chromatograph column;
   detecting the sample and standard as both exit the chromatograph column; and
   determining an integrity of the sample collection by comparing the detections of the sample with the detections of the standard.

2. The method as set forth in claim 1 wherein the standard material is a standard gas of known quantity and composition.

3. The method as set forth in claim 1 wherein transferring the analyte of the sample gas and the compound of the standard gas to the analytical instrument comprises transferring the analyte of the sample gas and the compound of the standard gas to the analytical instrument in flow with a carrier gas.

4. The method as set forth in claim 1 further comprising venting the carrier gas from the first vessel.

5. The method as set forth in claim 4 wherein transferring the analyte of the sample gas and the compound of the standard gas to the analytical instrument comprises desorbing the compound of the standard gas and the analyte of the sample gas from the first vessel.

6. The method as set forth in claim 5 wherein desorbing the compound of the standard gas and the analyte of the sample gas comprises thermally desorbing the compound of the standard gas and the analyte of the sample.

7. The method as set forth in claim 1 wherein the compound of the standard gas comprises one or more compounds not present in the analyte of the sample gas and of similar quantity and composition to the analyte of the sample gas.

8. The method as set forth in claim 1 further comprising:
   separating an analyte of the sample gas from a compound of the standard gas;
   determining the mass spectrum of the compound of the standard gas; and
   comparing the mass spectrum of the compound of the standard gas to a known mass spectrum of the compound of the standard gas.

9. The method as set forth in claim 8 further comprising:
   determining the mass spectrum of an analyte of the sample gas;
   comparing the mass spectrum of the analyte of the sample gas to a known mass spectrum of the analyte of the sample gas.

10. The method as set forth in claim 1 further comprising comparing intensities of individual mass spectra of the compound of the standard gas to a standard mass spectra of the compound of the standard gas.

11. The method as set forth in claim 1 further comprising introducing a second quantity of a standard gas into the first vessel wherein the second quantity of a standard gas is different than the first quantity of the standard gas.

12. The method as set forth in claim 11 wherein introducing a second quantity of a standard gas into the first vessel comprises introducing the second quantity of a standard gas into the first vessel after introducing a quantity of the sample gas into the first vessel and before transferring the analyte of the sample gas and a compound of the standard gas to the analytical instrument.

13. The method as set forth in claim 12 further comprising calibrating the analytical instrument so as to obtain a mass spectra of the second quantity of a standard gas comparable to a standard value thereof in a standard sample.

14. The method according to claim 1, further comprising introducing a second standard into the vessel before introduction into the chromatograph column.

15. The method according to claim 14, further comprising:
   introducing the standard, sample, and second standard into the chromatograph column;
   detecting the sample, standard, and second standard as all exit the chromatograph column; and
   determining an integrity of the sample collection by comparing the detections of the sample with the standard and second standard.

16. A method of transferring an analyte of a sample to an analytical instrument, the method comprising:
   first introducing a first quantity of a standard material into a first vessel containing an adsorbent material;
   then introducing a quantity of the sample into the first vessel; and
   transferring the analyte of the sample and a compound of the standard material to the analytical instrument via a carrier gas flow introduced after the sample is introduced into the vessel;
   selecting a standard having chromatographic detection characteristics indicative of the sample to be analyzed;
   introducing the standard into a vessel placed at a location of thermal desorption;
   transporting the vessel to a site remote from and separate from the location for collecting a sample, wherein the sample is mixed with the standard;
   transporting the vessel to the location;
   introducing the sample and standard into a chromatograph column;
   detecting the sample and standard as both exit the chromatograph column; and
   determining an integrity of the sample collection by comparing the detections of the sample with the detections of the standard.

* * * * *